(12) United States Patent
Detweiler et al.

(10) Patent No.: US 11,446,068 B2
(45) Date of Patent: Sep. 20, 2022

(54) DRIVEN UNIVERSAL SCREW GUIDE

(71) Applicant: Jace Medical, LLC, Warsaw, IN (US)

(72) Inventors: Jason F. Detweiler, Warsaw, IN (US);
Scott Steffensmeier, Roanoke, IN (US)

(73) Assignee: Jace Medical, LLC, Warsaw, IN (US)

( * ) Notice: Subject to any disclaimer, the term of this patent is extended or adjusted under 35 U.S.C. 154(b) by 0 days.

(21) Appl. No.: 17/117,604

(22) Filed: Dec. 10, 2020

(65) Prior Publication Data
US 2021/0177472 A1  Jun. 17, 2021

Related U.S. Application Data

(60) Provisional application No. 62/947,570, filed on Dec. 13, 2019.

(51) Int. Cl.
*A61B 17/80* (2006.01)
*A61B 17/88* (2006.01)
*A61B 17/90* (2006.01)

(52) U.S. Cl.
CPC ........ *A61B 17/808* (2013.01); *A61B 17/8085* (2013.01); *A61B 17/8875* (2013.01); *A61B 17/8894* (2013.01); *A61B 17/90* (2021.08)

(58) Field of Classification Search
CPC ..... A61B 17/808; A61B 17/865; A61B 17/88; A61B 17/8872; A61B 17/8875; A61B 17/888; A61B 17/8886; A61B 17/8888; A61B 17/8891; A61B 17/8894; A61B 17/90; B25B 17/00; B25B 17/02
See application file for complete search history.

(56) References Cited

U.S. PATENT DOCUMENTS

| 4,140,161 | A | * | 2/1979 | Russo | .................... B25B 23/10 81/451 |
| 5,190,545 | A | | 3/1993 | Corsi et al. | |
| 6,007,538 | A | | 12/1999 | Levin | |
| 6,012,359 | A | * | 1/2000 | Lin | .......................... F16H 1/28 81/57.12 |
| 6,244,141 | B1 | * | 6/2001 | Han | ....................... B25B 23/10 81/453 |
| 7,588,576 | B2 | | 9/2009 | Teague et al. | |
| 8,414,594 | B2 | | 4/2013 | Berger et al. | |
| 10,159,503 | B2 | * | 12/2018 | Niederberger | ..... A61B 17/8057 |
| 10,307,193 | B2 | | 6/2019 | Garcia et al. | |
| 10,758,290 | B2 | | 9/2020 | Detweiler et al. | |
| 10,772,666 | B2 | * | 9/2020 | Johnston, Jr. | ........ A61B 17/808 |
| 2010/0274249 | A1 | | 10/2010 | Dell'Oca | |
| 2018/0177510 | A1 | | 6/2018 | Whitaker et al. | |
| 2021/0113255 | A1 | * | 4/2021 | Stockdill | ............. A61B 17/808 |

FOREIGN PATENT DOCUMENTS

JP  3106821 U  11/2004

* cited by examiner

*Primary Examiner* — Larry E Waggle, Jr.
(74) *Attorney, Agent, or Firm* — Schwegman Lundberg & Woessner, P.A.

(57) ABSTRACT

A driven fastener guide for guiding a fastener into a hole of a bone plate. The driven fastener guide includes an elongated driver configured for connecting to a drill and a fastener guide member operably connected to the elongated driver. The fastener guide member includes a split body and a through-bore configured for receiving the fastener. The fastener guide member is configured for aligning the fastener relative to the hole of the bone plate.

20 Claims, 14 Drawing Sheets

DRIVEN UNIVERSAL SCREW GUIDE

CROSS REFERENCE TO RELATED APPLICATIONS

This is a non-provisional application based upon U.S. provisional patent application Ser. No. 62/947,570, entitled "DRIVEN UNIVERSAL SCREW GUIDE", filed Dec. 13, 2019, which is incorporated herein by reference.

BACKGROUND OF THE INVENTION

1. Field of the Invention

The present invention relates generally to bone closure devices for securing bone portions together, and more particularly, to a driven screw guide for use with a bone plate.

2. Description of the Related Art

Some surgical procedures involve separating a bone into portions and reuniting the bone portions after conducting the desired operation within the body. Various devices are used to refix or resecure the bone portions to one another. For example, in a sternal reapproximation medical procedure, one or more sternal fixation or closure devices can be used to hold and secure the portions of the sternum together. Generally, each sternal fixation device will engage or otherwise wrap around the sternal portions in order to hold and secure the sternal portions together. One such fixation device is a bone plate with one or more threaded holes for receiving bone screws therein. The bone plate spans across the bone portions, and upon screwing the bone screws into the bone portions, the bone plate holds the bone portions together.

A positioning device or screw guide may be used in conjunction with a bone plate to help guide the bone screw into the bone plate. A typical screw guide includes a screw cartridge with multiple screws therein and a tubular body with a channel or through-bore. The channel of the screw guide receives the screw, from the cartridge, and guides the bone screw to the desired threaded hole in the bone plate. The screw guide may also guide the screwdriver or drill bit which screws the bone screw into the threaded hole of the bone plate.

What is needed in the art is a screw guide multitool for collectively retaining, guiding, and driving a screw into a bone plate.

SUMMARY OF THE INVENTION

The present invention provides a multitool in the form of a driven fastener guide that collectively retains a fastener therein, secures itself relative to a bone plate, aligns the fastener to the desired hole of the bone plate, and drives the fastener into the bone plate. The driven fastener guide includes an elongated driver configured for connecting to a drill and a fastener guide member operably connected to the elongated driver. The fastener guide member includes a split body and a through-bore configured for receiving the fastener. The fastener guide member is configured for aligning the fastener relative to the hole of the bone plate.

The invention in one form is directed to a driven fastener guide for guiding a fastener into a hole of a bone plate. The driven fastener guide includes an elongated driver configured for connecting to a drill and a fastener guide member operably connected to the elongated driver. The fastener guide member includes a split body and a through-bore configured for receiving the fastener. The fastener guide member is configured for aligning the fastener relative to the hole of the bone plate.

The invention in another form is directed to a method for securing bone portions of an individual. The method includes an initial step of providing a driven fastener guide. The driven fastener guide is configured for guiding a fastener into a hole of a bone plate. The driven fastener guide includes an elongated driver configured for connecting to a drill and a fastener guide member operably connected to the elongated driver. The fastener guide member includes a split body and a through-bore configured for receiving the fastener. The method further includes inserting the fastener into the through-bore of the split body. The method further includes aligning the fastener relative to the hole of the bone plate by screwing the fastener guide member into the hole of the bone plate. The method further includes simultaneously unscrewing the fastener guide member from the hole of the bone plate and screwing the fastener into the hole of the bone plate.

An advantage of the present invention is that the driven fastener guide collectively retains, aligns, and inserts the fastener into the desired hole of the bone plate.

Another advantage of the present invention is that the driven fastener guide simultaneously unscrews the fastener guide member and inserts the fastener within the hole of the bone plate so that the fastener does not become misaligned.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 5:
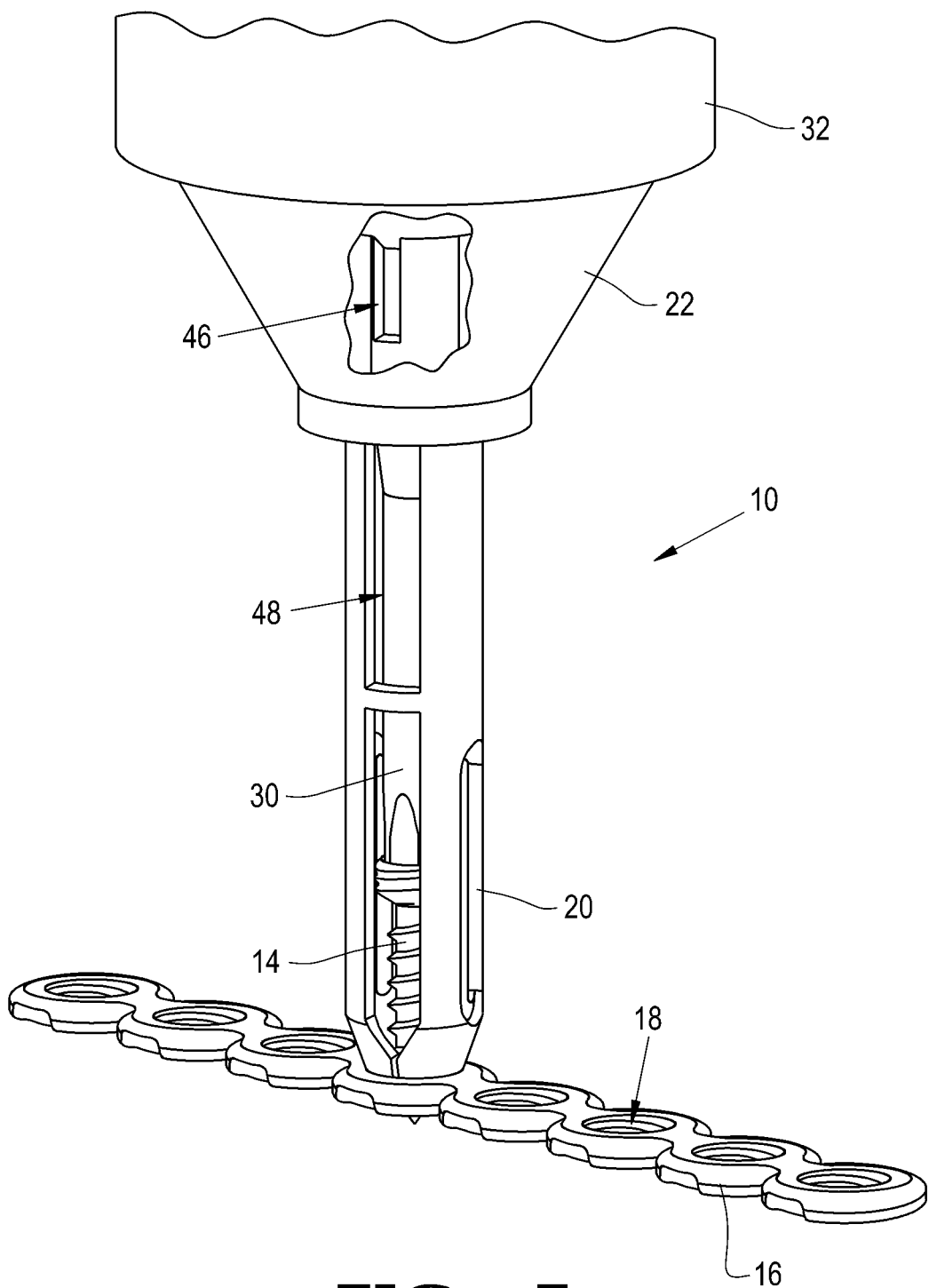
FIG. 5 is a perspective view of the end of the screw guide driver of FIG. 1, wherein the screw guide driver is shown to be attached to the bone plate and the screw is positioned within the screw guide.
Figure 6:
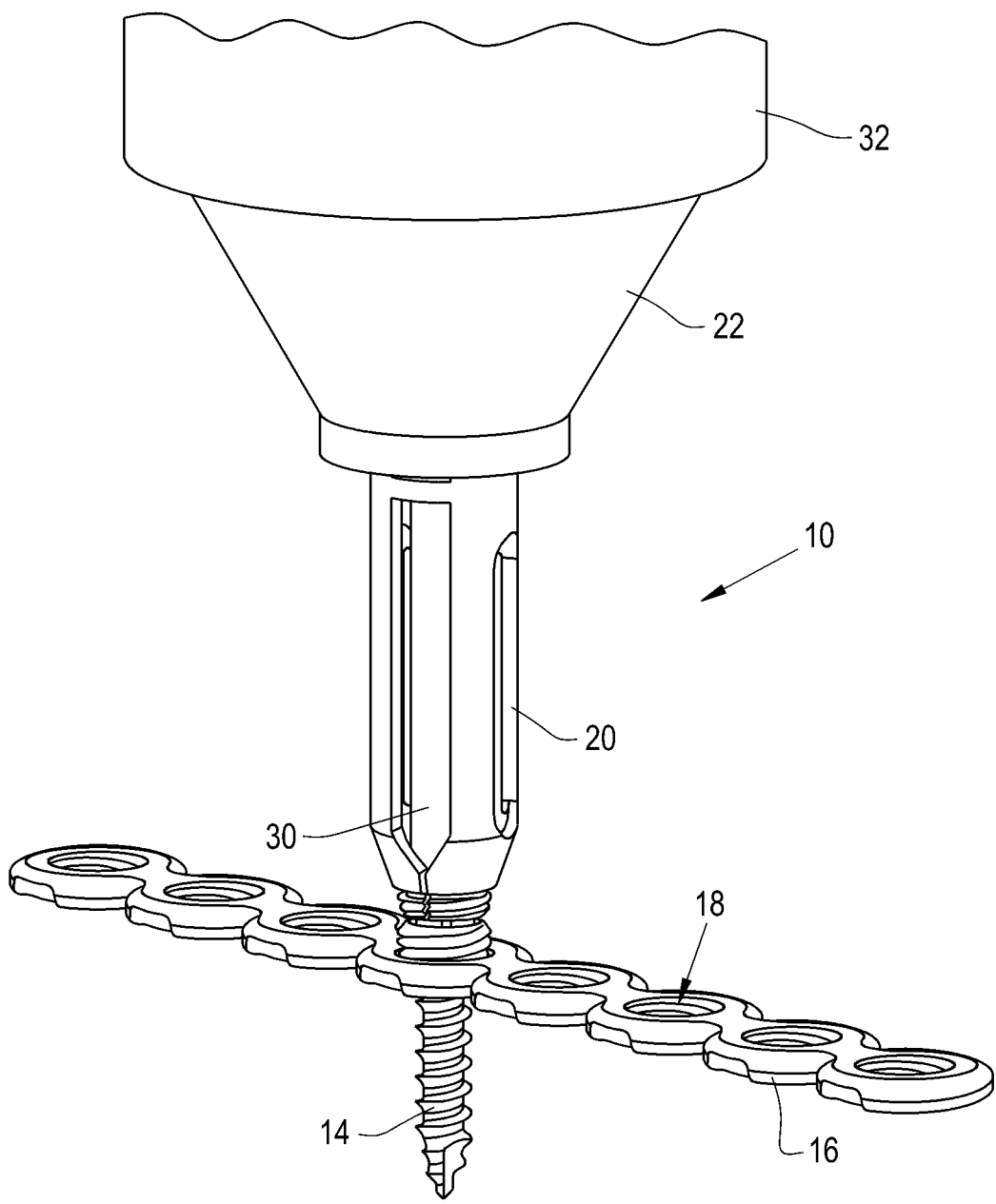
FIG. 6 is a perspective view of the end of the screw guide driver of FIG. 1, wherein the screw guide driver is shown to be attached to the bone plate and the screw is seated within the bone plate.
Figure 7:
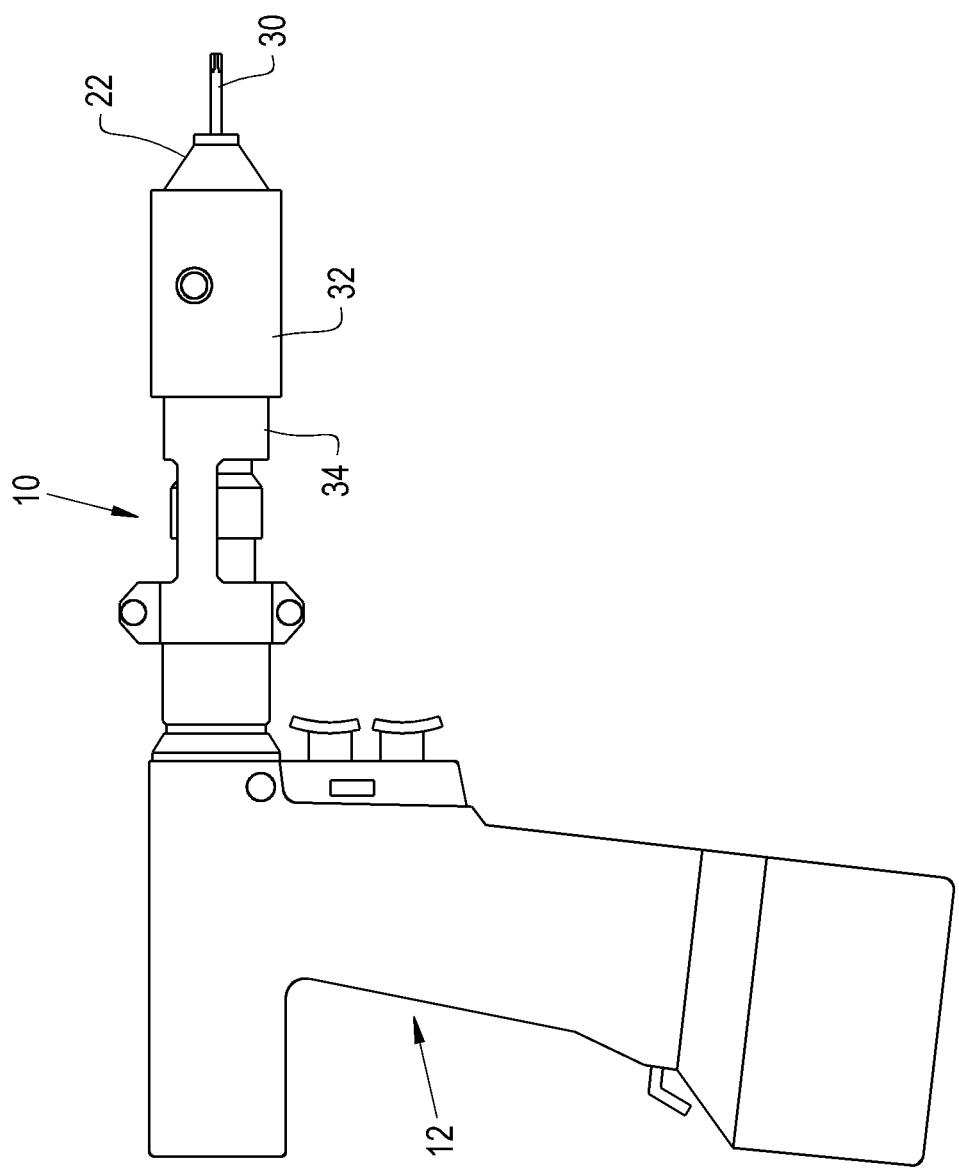
FIG. 7 is a side view of a drill with the screw guide driver of FIGS. 1-6 attached thereto.

Referring now to the drawings, and more particularly to FIGS. 1-7, there is shown a driven fastener guide 10 which is driven by a handheld driver, such as an electric drill 12 (FIG. 7). The driven fastener guide 10 is capable of collectively holding, guiding, and inserting fasteners 14 into variously configured fixation devices 16, such as bone plates 16. The driven fastener guide 10 is also capable of removing and holding fasteners 14 therein. In operation, the driven fastener guide 10 may removably engage with the bone plate 16 for easily guiding the fastener 14 into or out of the bone plate 16. The fastener 14 may be in the form of a bone screw 14. Alternatively, the fastener 14 may be in the form of a marking device, a peg, a headless pin, etc.

Alternatively to being driven by an electric drill 12, the driven fastener guide 10 may be manually driven. For instance, the driven fastener guide 10 may connect to a handle portion for allowing a user to manually rotate the driven fastener guide 10. The driven fastener guide 10 may comprise any desired material, such as metal and/or plastic. Thereby, the drill 12 may be in the form of any desired electric and/or manually operated drill 12.

The driven fastener guide 10 generally includes a deformable stem or fastener guide member 20, a stem mounting member 22 which may be in the form of a collar 22, a gearing assembly including a gear mount 24 which mounts multiple gears 26, 28 thereon, an elongated driver 30 operably connected to the gears 26, 28, and a housing or casing 32. After inserting a fastener 14 into the fastener guide member 20, the driven fastener guide 10 may initially align the fastener 14 by engaging, e.g. screwing, the end of the fastener guide member 20 with the bone plate 16. Thereafter, the driven fastener guide 10 may simultaneously disengage the fastener guide member 20 and insert the fastener 14 within the bone plate 16. For instance, the elongated driver 30 and the collar 22 may simultaneously rotate in opposite directions in order to unscrew the fastener guide member 20 from the hole 18 which allows the bone screw 14 to pass through the fastener guide member 20 and be accordingly screwed into the hole 18. The driven fastener guide 10 may be considered a universal driver 10 since it does not require the bone plate 16 to have any additional or separate mating features other than the existing threaded through hole 18 itself.

The driven fastener guide 10 may also include a drill mount 34 that is removably connected to the drill 12 by way of a clamping mechanism. The drill mount 34 is connected to the housing 32 and thus removably connects the housing 32 to the drill 12 by way of the clamping mechanism. The drill mount 34 provides a stable and sturdy connection between the housing 32 and the drill 12. It should be appreciated that the driven fastener guide 10 may not include the drill mount 34 such that only the elongated driver 30 is operably coupled to the drill 12. In such a configuration, the user may manually hold onto the housing 32 to make the collar 22 spin in reverse. Also, the driven fastener guide 10 may be fixedly attached to the drill 12.

Figure 4:
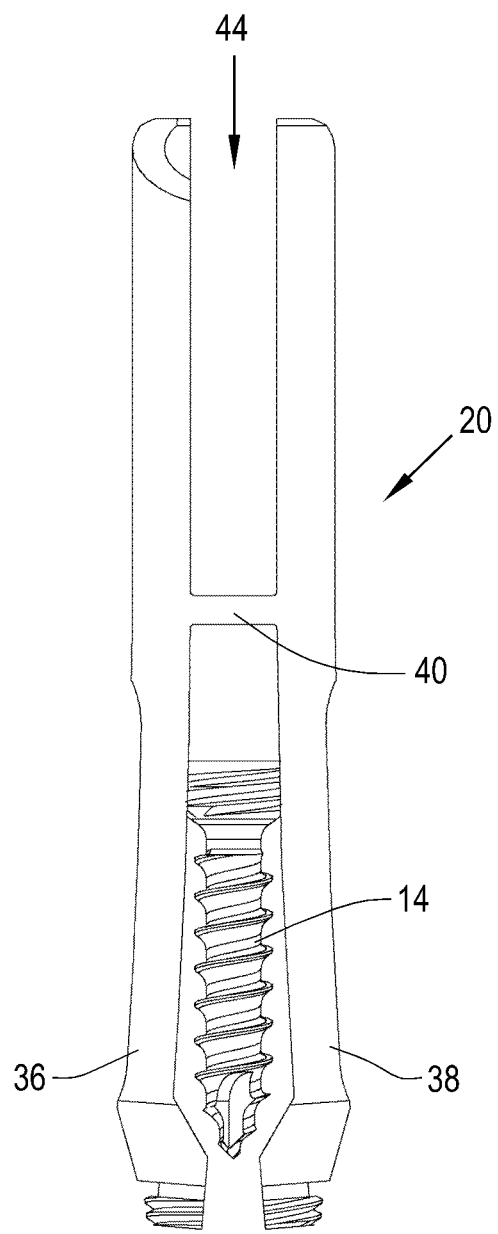
FIG. 4 is a side view of the deformable end of the screw guide driver of FIG. 1.

The fastener guide member 20 holds and guides the screw 14. The fastener guide member 20 also aligns the screw 14 by threading into, or otherwise engaging, the hole 18 of the bone plate 16. The fastener guide member 20 generally includes a split body 36, 38, 40, 42. The split body includes left and right portions 36, 38, a connecting member 40 which connects the two portions 36, 38 together, and one or more beams 42 for engaging with and temporarily holding the screw 14 within the internal cavity or through-bore 44 of the fastener guide member 20 (FIG. 4). The split body of the fastener guide member 20 includes an upper end which is engageable with the collar 22 and a lower threaded end which is engageable with the threaded hole 18 of the bone plate 16. It is noted that lower end of the split body may or may not be threaded. It should be appreciated that the fastener guide member 20 may guide the screw 14 and/or any desired tool or device. For instance, the fastener guide member 20 may be used to guide bone preparation tools, e.g. drills or taps, prior to insertion of the screw 14 into the fastener guide member 20. The fastener guide member 20 may comprise any desired material such as a deformable material, including metal and/or plastic.

The fastener guide member 20 is operably connected to the elongated driver 30 by way of the collar 22. The fastener guide member 20 may be removably attached to the collar 22. For instance, the fastener guide member 20 can be press-fit within the collar 22, coupled to the collar 22 by one or more fasteners, have one or more mating features which selectively engage with corresponding mating features of the collar 22, and/or simply be received within the collar 22 without being permanently fixed to the collar 22. Additionally, for example, protrusions 46 inside the collar 22 may engage with corresponding removal slots 48 of the fastener guide member 20 (FIG. 5).

Figure 1:
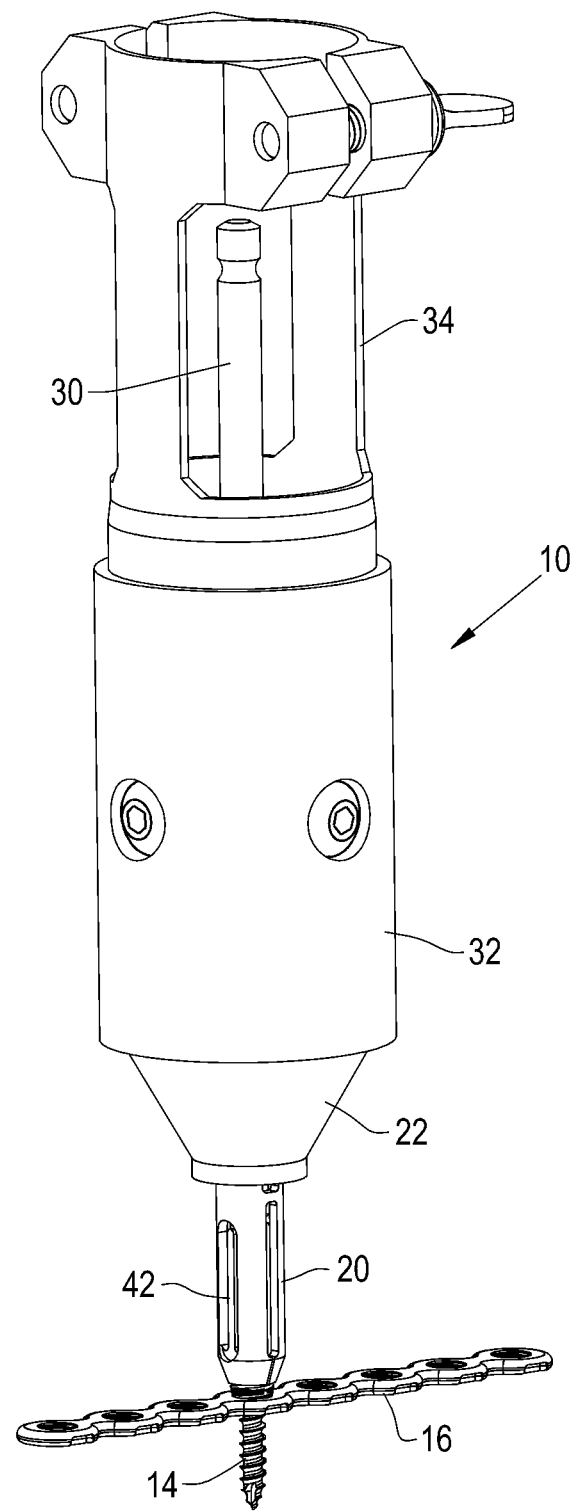
FIG. 1 is a perspective view of an embodiment of a universal screw guide driver for driving a screw into a bone plate, the screw guide driver includes a guide member, a collar, a gearing assembly, an elongated driver bit, and a housing.
Figure 2:
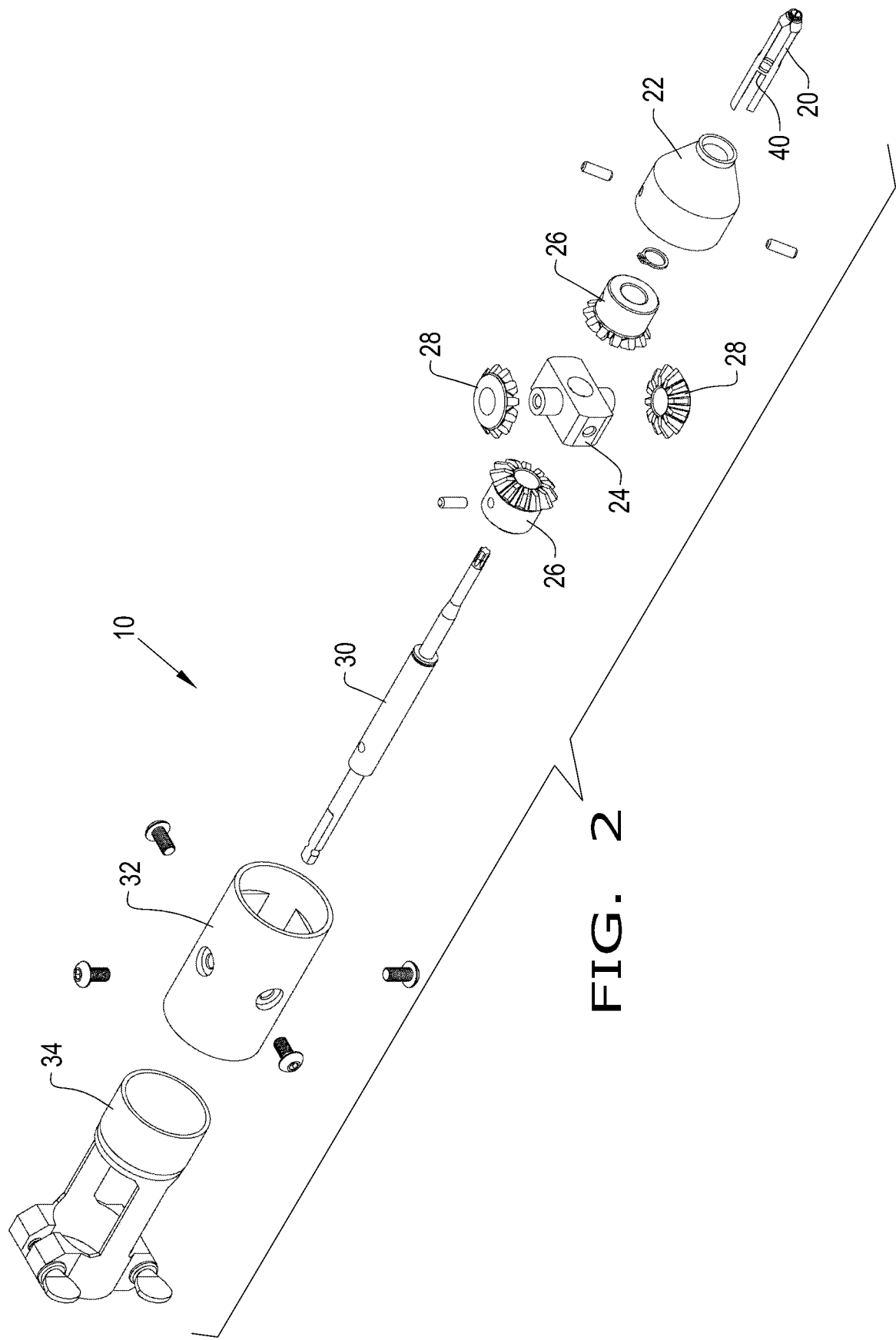
FIG. 2 is an exploded view of the screw guide of FIG. 1.

The portions 36, 38 may flex or bend relative to one another because the potions 36, 38 are only connected to one another by the connecting member 40 (FIGS. 2 and 4). In more detail, the connecting member 40 may comprise a pair of arcuate and substantially horizontal linking arms which rigidly link the portions 36, 38 together at an attachment point such that the portions 36, 38 may flex relative to the attachment point. The portions 36, 38 may be pressed or squeezed together to allow the fastener guide member 20 to be screwed into the hole 18 of the bone plate 16. Additionally, for example, the portions 36, 38 may be flexed outwardly or separated from one another. The user may manually flex the portions 36, 38 outwardly and/or upon inserting a screw 14 into the fastener guide member 20, the portions 36, 38 may automatically flex outwardly by way of the force of the screw 14 acting against the inner walls of the portions 36, 38. Hence, an opening or gap between the portions 36, 38 may widen for allowing the screw 14 to enter or exit the fastener guide member 20. In this regard, the internal walls of the portions 36, 38 may contact the screw 14 for applying a retaining force onto the screw 14 to retain the screw within the cavity 44 of the fastener guide member 20. It should be appreciated that the connecting member 40 may be in the form of a pin or hinge member which allows the portions 36, 38 to pivot relative to one another.

The one or more beams 42, i.e., retaining members, may be located on the portions 36, 38. More particularly, one or both of the portions 36, 38 may have a slot in its side with the beam 42 extending upwardly from the bottom of the slot.

Each beam 42 may extend upwardly and inwardly such that each beam 42 at least partially extends into the cavity 44 of the fastener guide member 20 to cause interference with, i.e., contact, the screw 14. Thereby, each beam 42 may help hold the screw 14 within the cavity 44 of the fastener guide member 20 by way of contacting and applying a retention force onto a side of the screw 14. Applying a downward force on the screw 14, by the elongated driver 30, will force the beam(s) 42 outwardly so that the screw 14 may pass through the fastener guide member 20. As can be appreciated, each beam 42 may be machined from a sidewall of the fastener guide member 20 such that the bottom of the beam 42 remains coupled with main body of the fastener guide member 20 and the top of the beam 42 is free to extend inwardly into the cavity 44 of the fastener guide member 20. Each beam 42 may extend at least partially, for example substantially, along the length of the fastener guide member 20. It should be appreciated that the fastener guide member 20 may not include any beams 42.

The collar 22 may be connected to the housing 32 and a gear 26 via one or more fasteners, such as pins, screws, bolts, etc. The collar 22 may also removably mount the fastener guide member 20. For instance, the collar 22 and the fastener guide member 20 may each include a corresponding mating feature, e.g. corresponding groove(s) and protrusion(s). Additionally, the collar 22 could also be fitted with a retaining feature, e.g. magnet, ball detent, etc., to retain the fastener guide member 20 and prevent unattended disassociation between the collar 22 and the fastener guide member 20. The collar 22 may also at least partially house any one of the gears 26, 28. The collar 22 may comprise any desired material such as metal and/or plastic.

The gearing assembly of the driven fastener guide 10 may generally include the gear mount 24, a pair of sun gears 26 in the form of input and output gears 26 mounted on the elongated driver 30, and a pair of intermediary, i.e., planetary gears 28 rotatably mounted onto the gear mount 24. The gear mount 24 has a center through hole for receiving the elongated driver 30 and a pair of protrusions which mount the planetary gears 28. The proximal, input gear 26 may be fixedly attached to the elongated driver 30 via one or more fasteners. The distal, output gear 26 may be coupled to the collar 22 via one or more fasteners. The rotary motion which is inputted by the elongated driver 30 is operably reversed by the gears 26, 28 so that the collar 22, and fastener guide member 20 therewith, rotate in an opposite direction to the elongated driver 30. The driven fastener guide 10 may include any number of gears. The gear ratio may be such that the fastener guide member 20 spins faster or slower than the elongated driver 30. Alternatively, the driven fastener guide 10 may include dual motors for generating the opposition rotation of the fastener guide member 20 and elongated driver 30.

The elongated driver 30 has one end for connecting to the drill 12 and an opposite end for connecting to the screw 14. The elongated driver 30 may also contact and/or mount the gear mount 24 and the gears 26, 28. The elongated driver 30 may also movably engage with the collar 22 via one or more bearings. The elongated driver 30 may be in the form of a drill bit 30. It should be appreciated that the end of the elongated driver 30 may have any desired configuration for engaging with any desired screw 14.

Figure 3:
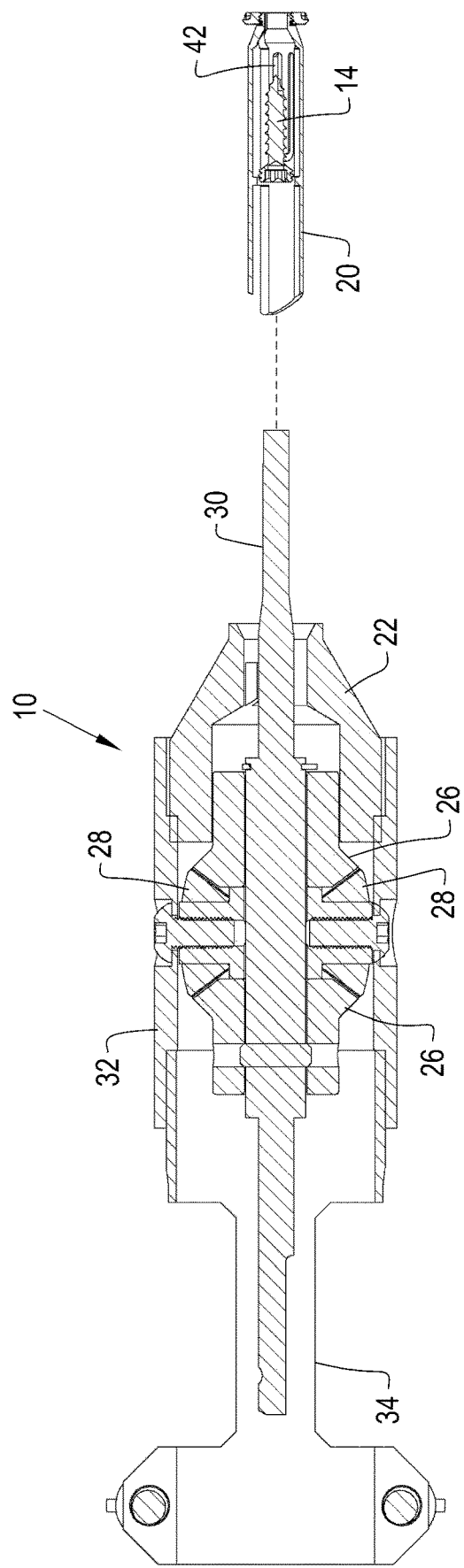
FIG. 3 is a cross-sectional view of the screw guide with the guide member being disconnected from the collar.

The housing 32 may be connected to the drill mount 34. The housing 32 may extend over at least a portion of the drill mount 34 and the collar 22, respectively (FIG. 3). The housing 32 may have a substantially tubular body with a circular cross-section. The housing 32 may also have internal grooves and/or protrusions for securing or otherwise accommodating the drill mount 34, the gears 26, 28, and/or the collar 22.

In operation, the user initially places a screw 14 inside of the fastener guide member 20. The one or more beams 42 may hold the screw 14 within the fastener guide member 20. Since the fastener guide member 20 is not attached to the driven guide 10, the user may position the fastener guide member 20 in the bone plate 16 before positioning the driven guide 10. For instance, the user may press the portions 36, 38 of fastener guide member 20 together and screw the fastener guide member 20 into the hole 18 of the bone plate 16 (FIG. 5). Additionally, the user may insert multiple fastener guide members 20 into respective holes 18 in the bone plate 16; thus, pre-aligning numerous screws 14 which are ready to be inserted into the bone via the driven guide 10. Then, the user will position the driven fastener guide 10 above a respective fastener guide member 20. The user may start drill 12 in a clockwise direction and advance the screw 14 into the bone through the hole 18 of the bone plate 16. Before the screw head seats in the bone plate 16, the collar 22 engages the fastener guide member 20 and starts to unscrew the fastener guide member 20 from the bone plate 16. In other words, prior to the screw 14 completely seating in the hole 18, protrusions 46 inside the collar 22 will engage the removal slots 48 of the fastener guide member 20 and rotate fastener guide member 20 in a counterclockwise direction and out of the hole 18 (FIG. 5). It is noted that the screw 14 applies a force onto the inner walls of the fastener guide member 20 so that the portions 36, 38 expand away from one another as the screw 14 is driven downwardly. With the fastener guide member 20 being disassociated from the hole 18, the screw 14 can be fully seated in hole 18 (FIG. 6). Hence, the fastener guide member 20 is fully removed in time to allow the screw head to pass completely through the fastener guide member 20 and into the bone plate 16. Thereby, screw alignment is advantageously maintained since the screw 14 is substantially inserted into the bone before the fastener guide member 20 is removed from the bone plate 16.

Referring now to FIGS. 8-14, there is shown a driven, multipart driven guide 50 for guiding and inserting fasteners 14 into variously configured bone plates 16 which may not have mating features for engaging with the driven guide 50. The driven guide 50 is attachable to a handheld drill 12. The driven guide 50 generally includes an outer sleeve 52, a split stem or fastener guide member 54, a flexible spacer 56 coupled to the stem 54, and a biasing member 58 connected in between the outer sleeve 52 and the stem 54. An elongated driver 60 can be inserted into and engaged with the driven guide 50 so that the stem 54 may be initially screwed into a desired hole 18 of the bone plate 16. As the elongated driver 60 drives or pushes the screw 14 downwardly toward the bone plate 16, the stem 54 will move upwardly away from the bone plate 16, and the elongated driver 60 may be subsequently driven to thread the screw 14 inside the hole 18 of the bone plate 16.

The outer sleeve 52 is movably connected to the stem 54. The outer sleeve 52 may generally include a substantially cylindrical body with an upper end and a lower end. The inside surface of the upper end may contact the upper end of the stem 54. The lower end may contact the bone plate 16. The body may also include one or more side openings and one or more inwardly extending mounting protrusions 62 for mounting and supporting the biasing member 58. Therein, the outer sleeve 52 may be movably connected to the stem 54 by way of the biasing member 58 which is connected in between corresponding protrusions 62, 64 of the outer sleeve 52 and the stem 54. The outer sleeve 52 may comprise any desired material.

Figure 13:
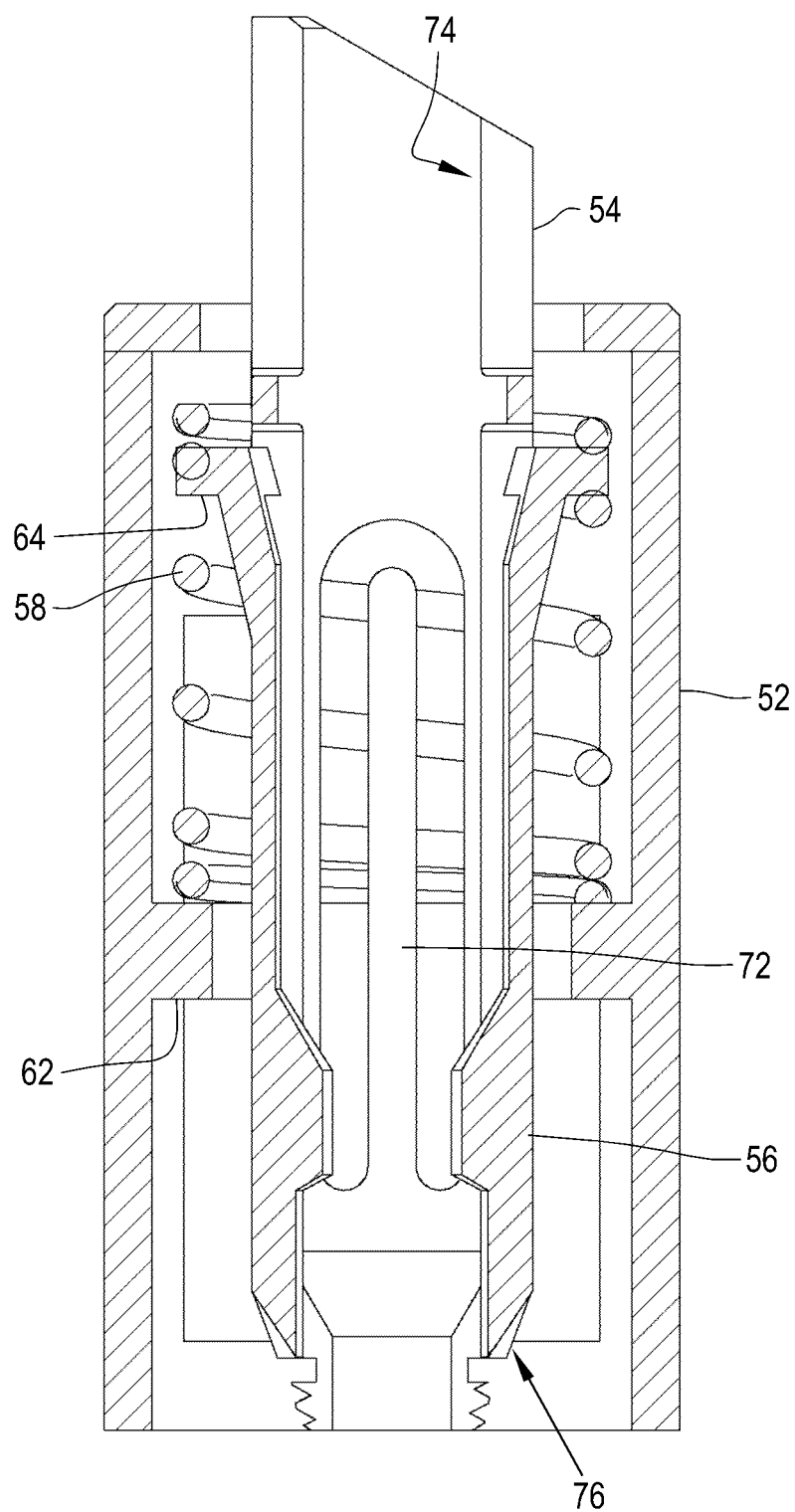
FIG. 13 is a cross-sectional view of the screw guide, taken across line 13-13 of FIG. 12.
Figure 14:
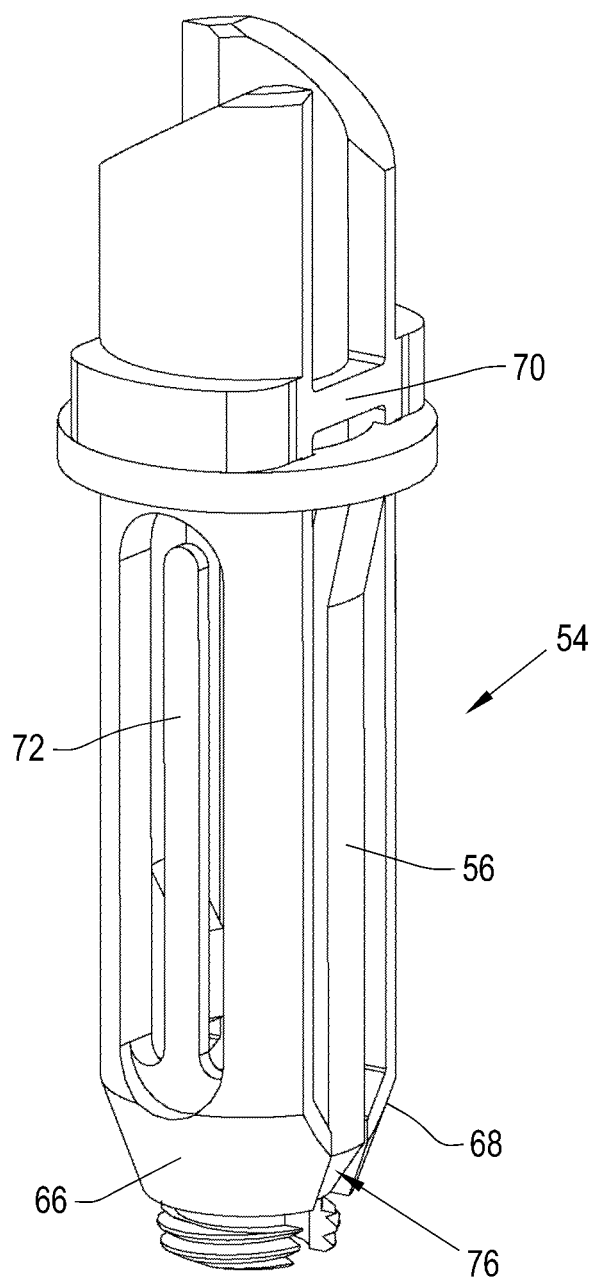
FIG. 14 is a perspective view of the split stem of the screw guide of FIGS. 8-13.

The stem 54 is operably connected to the elongated driver 60. The stem 54 is also movably connected to the outer sleeve 52. The stem 54 includes an upper end that selectively contacts the outer sleeve 52 and a lower end that is engageable with the bone plate 16. The upper end has one or more inwardly extending mounting protrusions 64 for engaging with the biasing member 58. The stem 54 includes a split body with left and right portions 66, 68, a connecting member 70 which connects the two portions 66, 68 together, and one or more beams 72 for engaging with and temporarily holding the screw 14 within the internal cavity or through-bore 74 of the stem 54 (FIGS. 13-14). The stem 54 is configured for temporarily housing the screw 14 and removably connecting to the hole 18 of the bone plate 16 so that the screw 14 may be aligned with and easily inserted into the hole 18. It should be appreciated that the stem 54 may also be used to guide bone preparation tools, e.g. drills, traps, etc. The one or more beams 72 may be designed and function similarly to the one or more beams 42, as discussed above. The stem 54 may comprise any desired material such as a deformable material, including metal and/or plastic.

The flexible spacer 56 is connected to the stem 54 and extends at least partially in between the portions 66, 68 of the stem 54 in order to prevent the portions 66, 68 from collapsing inwardly relative to one another. Meaning, in at least one location, a portion of the flexible spacer 56 extends at least partially in between the portions 66, 68 of the stem 54 to prevent the portions 66, 68 from moving inwardly toward each other. As shown, the flexible spacer 56 has a split body with two body portions that respectively fit within both of the spaces or slits in between the portions 66, 68 of the stem 54 (FIG. 14). The flexible spacer 56 is configured for temporarily preventing the portions 66, 68 from collapsing so that the threaded end of the stem 54 can be screwed into the hole 18 of the bone plate 16. The flexible spacer 56 is also configured for flexing inwardly, which thereby allows the portions 66, 68 to collapse, i.e., move inwardly toward each other, so that the threaded end of the stem 54 can be disengaged from and lifted out of the hole 18 of the bone plate 16. The flexible spacer 56 has a body which is bent inwardly for contacting the head of the screw 14. In this regard, the flexible spacer 56 has a design which allows clearance with the shank of the screw 14 but interference with the head of the screw 14. The ends of the flexible spacer 56 each have a slanted shoulder 76. The slanted shoulders 76, upon contacting the hole 18 of the bone plate 16, cause the flexible spacer 56 to flex in order to allow the portions 66, 68 of the stem 54 to collapse (FIG. 13). For instance, the flexible spacer 56 may flex outwardly in order to allow the stem 54 to accordingly collapse. The flexible spacer 56 may comprise any desired material, such as a deformable material, including metal and/or plastic.

The biasing member 58 is located in between the protrusions 62, 64 of the outer sleeve 52 and the stem 54. The biasing member 58 is configured for lifting the stem 54 upwardly relative to the outer sleeve 52. In other words, the biasing member 58 biases the stem 54 to contact the inside surface of the upper end of the outer sleeve 52. The biasing member 58 may be in the form of any desired biasing member, such as a coil spring.

Figure 8:
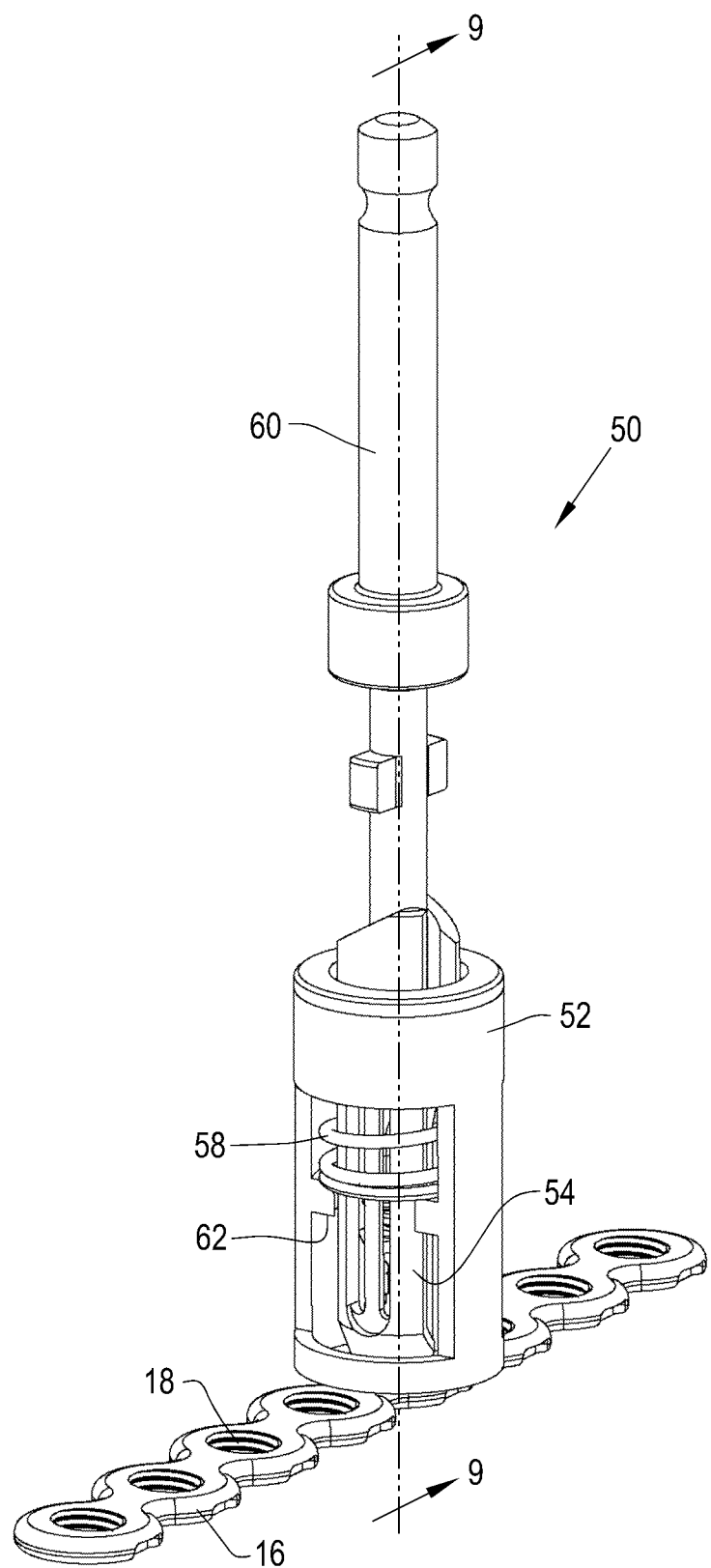
FIG. 8 is a perspective view of another embodiment of a multipart screw guide that is driven by a drill bit of a handheld drill, the screw guide includes an outer sleeve, a split stem, a flexible spacer, and a biasing member.
Figure 9:
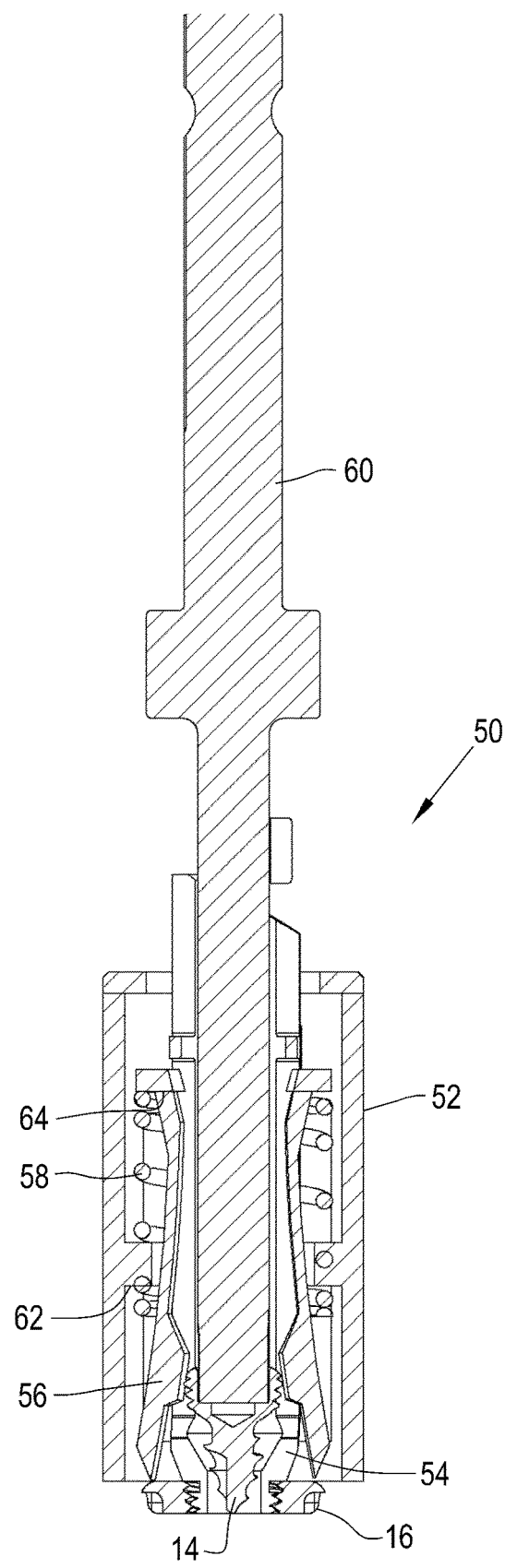
FIG. 9 is a cross-sectional view of the screw guide, taken across line 9-9 of FIG. 8.
Figure 10:
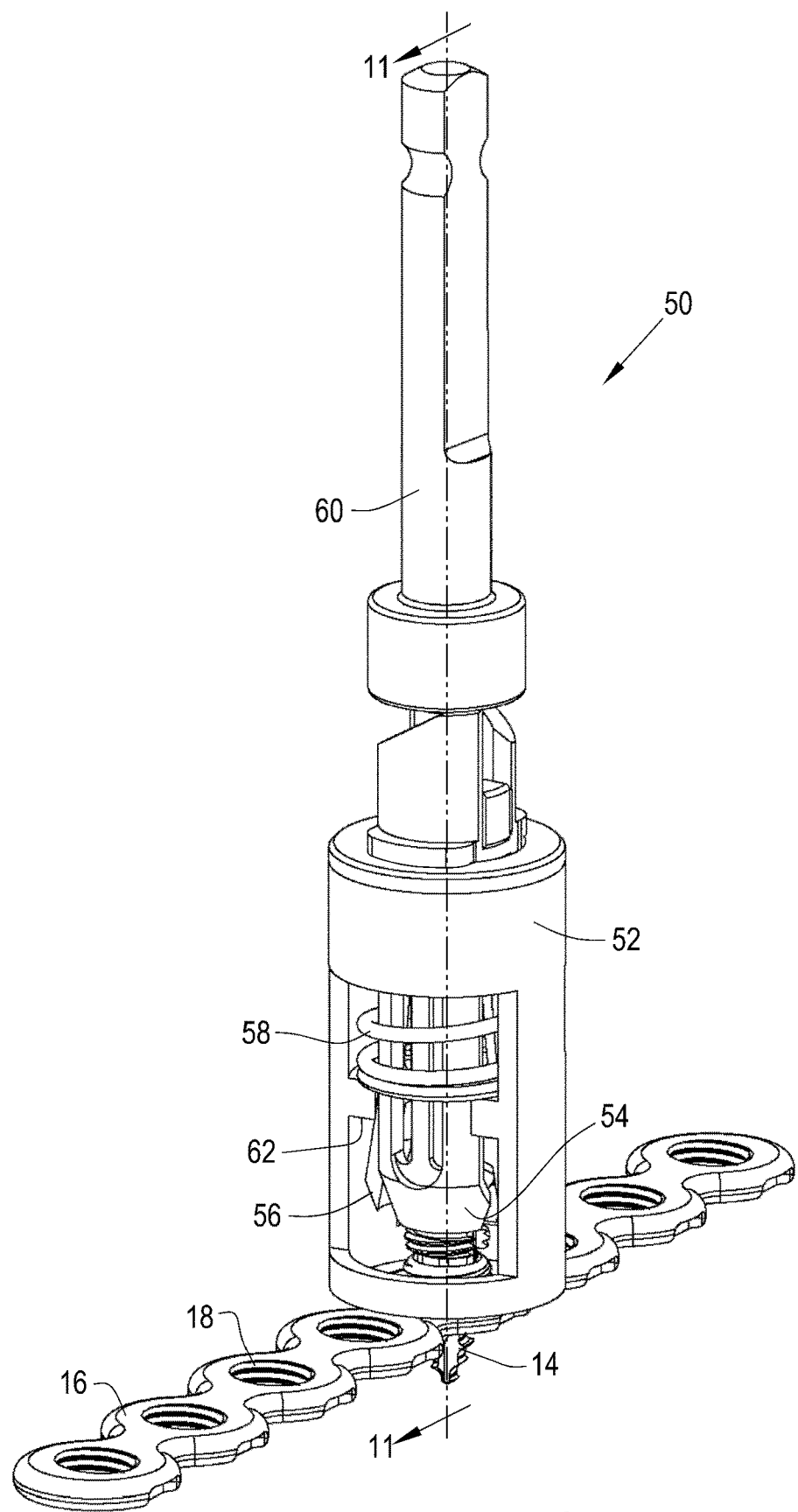
FIG. 10 is a perspective view of the screw guide, wherein the drill bit is engaged with the outer sleeve and the screw is seated within the bone plate.
Figure 11:
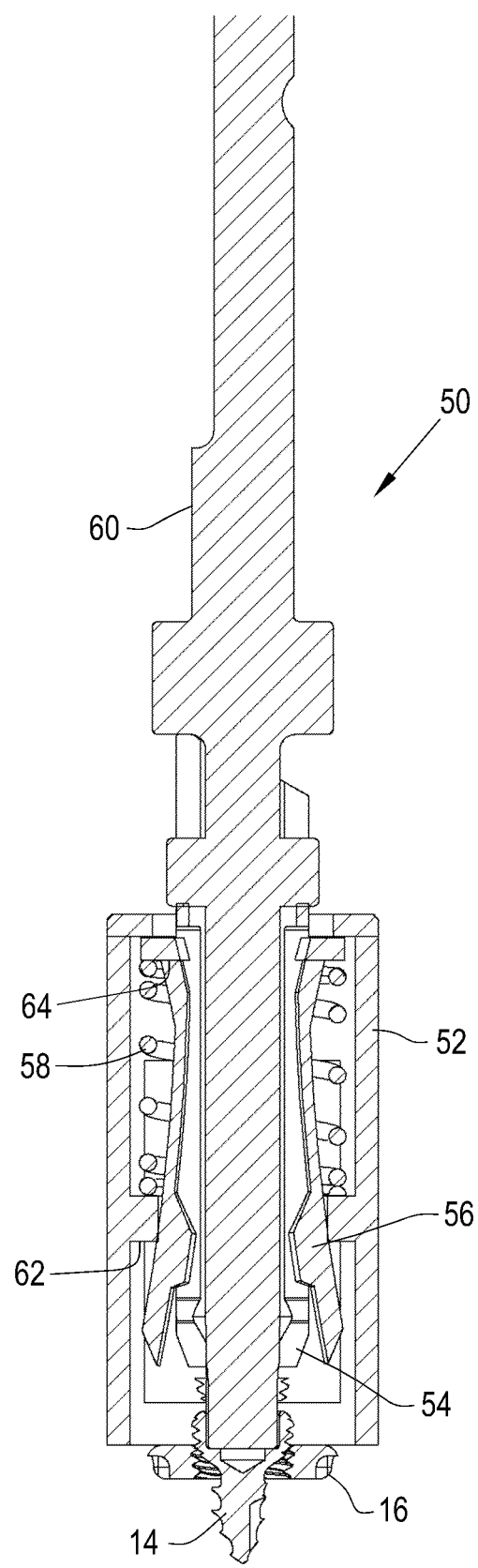
FIG. 11 is a cross-sectional view of the screw guide, taken across line 11-11 of FIG. 10.
Figure 12:
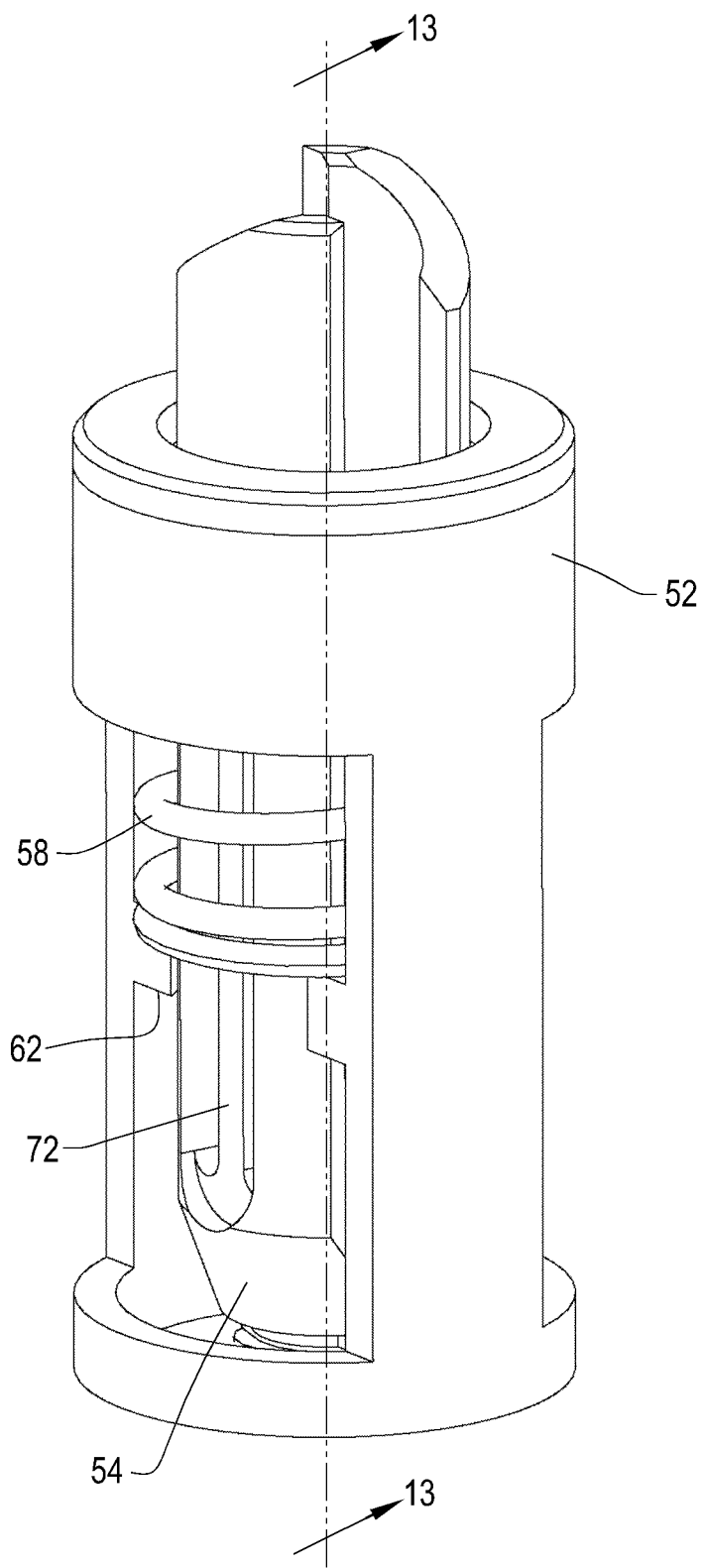
FIG. 12 is a perspective view of the screw guide of FIG. 8.

In operation, the user initially places a screw 14 inside of the stem 54. Then, the user will align the stem 54 with an empty hole 18 in the bone plate 16. The user will then push down on the stem 54 and thread the entire driven guide 50 into the bone plate 16 by way of the threaded end of the stem 54 (FIGS. 8-9). Then, the user will begin the process of screwing the screw 14 into the bone plate 16 (FIGS. 10-11). Since the flexible spacer 56 and stem 54 are split, the head of the screw 14 will flex the flexible spacer 56 outwardly as the screw 14 is advanced down the stem 54 such that the threaded end of the stem 54 is able to inwardly collapse. As the head of the screw 14 approaches the top of the bone plate 16, the bosses on the elongated driver 60 will engage the stem 54 and start turning the stem 54. The shoulder 76 of the flexible spacer 56 will dually prevent the stem 54 from advancing distally cause the threaded end of the stem 54 to collapse inwardly to disengage the stem 54 from the threads in the hole 18. Then, the biasing force of the biasing member 58 will lift the stem 54 upwardly since the stem 54 is no longer attached to the bone plate 16. With the stem 54 up and out of the way of the hole 18, the screw 14 can flex the threaded end of stem 54 outward to pass through stem 54 in order to be properly seated in the hole 18 of the bone plate 16. More particularly, the head of the screw 14 will push the portions 66, 68 and the flexible spacer 56 outwardly as the elongated driver 60 screws the screw 14 into the hole 18 of the bone plate 56.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A driven fastener guide for guiding a fastener into a hole of a bone plate, comprising:
    an elongated driver configured for connecting to a drill;
    a fastener guide member operably connected to the elongated driver, the fastener guide member comprising a split body and a through-bore configured for receiving the fastener, the fastener guide member being configured for aligning the fastener relative to the hole of the bone plate;
    a housing; and
    a plurality of gears housed within the housing and configured for being driven by the elongated driver, wherein the plurality of ears comprises an input gear fixedly connected to the elongated driver, an output gear, and a pair of intermediary gears connected in between the input gear and the output gear, wherein the pair of intermediary ears are configured for reversing direction of rotation such that the input gear and the output gear can rotate in opposite directions.

2. The driven fastener guide of claim 1, wherein the fastener guide member further comprises at least one retaining member configured for contacting and retaining the fastener within the split body.

3. The driven fastener guide of claim 2, wherein the at least one retaining member extends at least partially into the through-bore.

4. The driven fastener guide of claim 1, wherein the split body comprises a first portion having a first end, a second portion having a second end, and a connecting member connecting the first portion and the second portion together such that the first portion and the second portion are flexible relative to one another, wherein the first end and the second end are configured for contacting the bone plate to align the fastener relative to the hole of the bone plate.

5. The driven fastener guide of claim 4, wherein the first end of the first portion and the second end of the second portion are threaded and configured for being screwed into the hole of the bone plate for aligning the fastener relative to the hole of the bone plate and unscrewed from the hole of the bole plate upon inserting the fastener into the hole of the bone plate.

6. The driven fastener guide of claim 1 further comprising a collar fixedly connected to the output gear.

7. The driven fastener guide of claim 6, wherein the collar is engageable with the fastener guide member for rotating the fastener guide member in the same rotational direction as the collar when so engaged.

8. The driven fastener guide of claim 7, wherein a portion of the fastener guide member is receivable in the collar.

9. The driven fastener guide of claim 7, wherein, due to the plurality of gears and engagement of the collar with the fastener guide member, the elongated driver and the fastener guide member are able to rotate in opposite directions for simultaneously unscrewing the fastener guide member from the hole of the bone plate and screwing the fastener into the hole of the bone plate.

10. The driven fastener guide of claim 1, further comprising a drill mount connected to the housing, the drill mount being configured for removably and fixedly, mounting the housing to the drill.

11. A driven fastener guide for guiding a fastener into a hole of a bone plate, comprising:
an elongated driver configured for connecting to a drill;
a fastener guide member operably connected to the elongated driver, the fastener guide member comprising a split body and a through-bore configured for receiving the fastener, the fastener guide member being configured for aligning the fastener relative to the hole of the bone plate, wherein the split bod comprises a first portion having a first end, a second portion having a second end, and a connecting member connecting the first portion and the second portion together such that the first portion and the second portion are flexible relative to one another, wherein the first end and the second end are configured for engaging the bone plate to align the fastener relative to the hole of the bone plate; and
a flexible spacer connected to the fastener guide member and extending in between the first portion and the second portion, the flexible spacer being configured for temporarily preventing the first portion and the second portion from collapsing to facilitate initially engaging the first end and the second end with the hole of the bone plate and for inwardly flexing upon engaging with the hole of the bone plate such that the first portion and the second portion can collapse to facilitate subsequently disengaging the first end and the second end from the hole of the bone plate.

12. The driven fastener guide of claim 11, wherein the flexible spacer comprises a pair of ends having slanted shoulders such that the flexible spacer flexes inwardly upon engaging with the hole of the bone plate.

13. The driven fastener guide of claim 11, further comprising an outer sleeve surrounding and being movably connected to the fastener guide member, the outer sleeve being configured for contacting the bone plate.

14. The driven fastener guide of claim 13, further comprising a biasing member connected in between the outer sleeve and the fastener guide member, the biasing member surrounding the fastener guide member, the biasing member being configured for biasing the fastener guide member to contact the outer sleeve.

15. A method for securing bone portions of an individual, comprising:
providing or obtaining a bone plate and a driven fastener guide configured for guiding a fastener into a hole of the bone plate, the driven fastener guide comprising an elongated driver configured for connecting to a drill and a fastener guide member operably connected to the elongated driver, the fastener guide member comprising a split body and a through-bore with the fastener received therein and aligned relative to the hole of the bone plate via a threaded connection between the fastener guide member and the hole of the bone plate; and
rotating the elongated driver in a first rotational direction to thereby simultaneously cause via said rotating: (i) the fastener to rotate in the first rotational direction to screw the fastener into the hole of the bone plate; and (ii) the fastener guide member to rotate in a second rotational direction opposite the first rotational direction to unscrew the fastener guide member from the hole of the bone plate.

16. The method of claim 15, wherein the driven fastener guide further comprises at least one retaining member contacting and applying a retaining force onto the fastener to retain the fastener within the split body.

17. The method of claim 16, wherein during screwing the fastener into the hole of the bone plate, the fastener moves downwardly through the through-bore and overcomes the retaining force applied by the at least one retaining member.

18. The method of claim 16, wherein the at least one retaining member extends at least partially into the through-bore.

19. The method of claim 15, wherein the split body comprises a first portion having a first end, a second portion having a second end, and a connecting member connecting the first portion and the second portion together such that the first portion and the second portion are flexible relative to one another, wherein the first end and the second end are configured for screwing into the hole of the bone plate to align the fastener relative to the hole of the bone plate.

20. The method of claim 15, wherein the driven fastener guide further comprises a housing and a plurality of gears housed within the housing and configured for being driven by the elongated driver, wherein the plurality of gears comprises an input ear fixedly connected to the elongated driver, an output gear, and a pair of intermediary gears connected in between the input gear and the output gear, wherein the pair of intermediary gears are configured for reversing a direction of rotation such that the input gear and the output gear can rotate in opposite directions.

* * * * *

UNITED STATES PATENT AND TRADEMARK OFFICE
CERTIFICATE OF CORRECTION

PATENT NO. : 11,446,068 B2
APPLICATION NO. : 17/117604
DATED : September 20, 2022
INVENTOR(S) : Detweiler et al.

It is certified that error appears in the above-identified patent and that said Letters Patent is hereby corrected as shown below:

In the Claims

In Column 8, Line 48, in Claim 1, delete "ears" and insert --gears-- therefor

In Column 8, Line 52, in Claim 1, delete "ears" and insert --gears-- therefor

In Column 8, Line 52, in Claim 1, after "reversing", insert --a--

In Column 9, Line 28, in Claim 10, delete "fixedly," and insert --fixedly-- therefor In Column 9, Line 38, in Claim 11, delete "bod" and insert --body-- therefor In Column 10, Line 54, in Claim 20, delete "ear" and insert --gear-- therefor Signed and Sealed this
Fifteenth Day of November, 2022

Katherine Kelly Vidal
Director of the United States Patent and Trademark Office